United States Patent [19]

Mylrea et al.

[11] 4,176,660

[45] Dec. 4, 1979

[54] DISPOSABLE ESOPHAGEAL AND TRACHEAL MULTI-PROBES

[75] Inventors: Kenneth C. Mylrea, Tucson, Ariz.; Joseph Demer, Baltimore, Md.

[73] Assignee: University Patents, Inc., Norwalk, Conn.

[21] Appl. No.: 885,173

[22] Filed: Mar. 10, 1978

[51] Int. Cl.² ............................................. A61B 5/02
[52] U.S. Cl. ................................... 128/671; 128/696; 128/715; 128/2.05 S; 128/724; 128/2.06 E; 128/736; 128/2.08; 339/100
[58] Field of Search ................. 128/2.05 R, 2 R, 2 H, 128/2 K, 208, 2.05 S, 2.06 E, 2.1 E, 404, 418, 419 P, DIG. 4, DIG. 29; 339/96, 100

[56] References Cited

U.S. PATENT DOCUMENTS

| | | |
|---|---|---|
| 3,083,350 | 3/1963 | Mitthauer et al. .................. 339/100 |
| 3,499,435 | 3/1970 | Rockwell et al. ............... 128/2.06 E |
| 3,734,094 | 5/1973 | Calinog ............................ 128/206 E |
| 3,951,136 | 4/1976 | Wall ................................. 128/2.06 E |

FOREIGN PATENT DOCUMENTS 2003138  7/1971  Fed. Rep. of Germany ...... 128/2.06 E

OTHER PUBLICATIONS

Johnston et al. "Body Tissue Transducer", IBM TechnicalDisclosure Bulletin, vol. 6, No. 8, Jan. 1964, pp. 13-14.

Primary Examiner—Lee S. Cohen
Attorney, Agent, or Firm—Martin Novack

[57] ABSTRACT

A disposable esophageal probe incorporating the capability to detect ECG waveforms, heart sounds and to measure body core temperature is described. The probe incorporates a plastic tube with electrically conductive pathways embedded in its side walls thereby eliminating any lumen obstruction. Its distal end is enclosed by a rubber sheath which provides a diaphragm for the transmission of sounds into the lumen of the tube. An integral disposable connector assembly is provided at its proximal end to enable direct connection to be made to the plastic pathways and the lumen. A modification of the probe which allows it to monitor respiration rate is also described.

6 Claims, 6 Drawing Figures

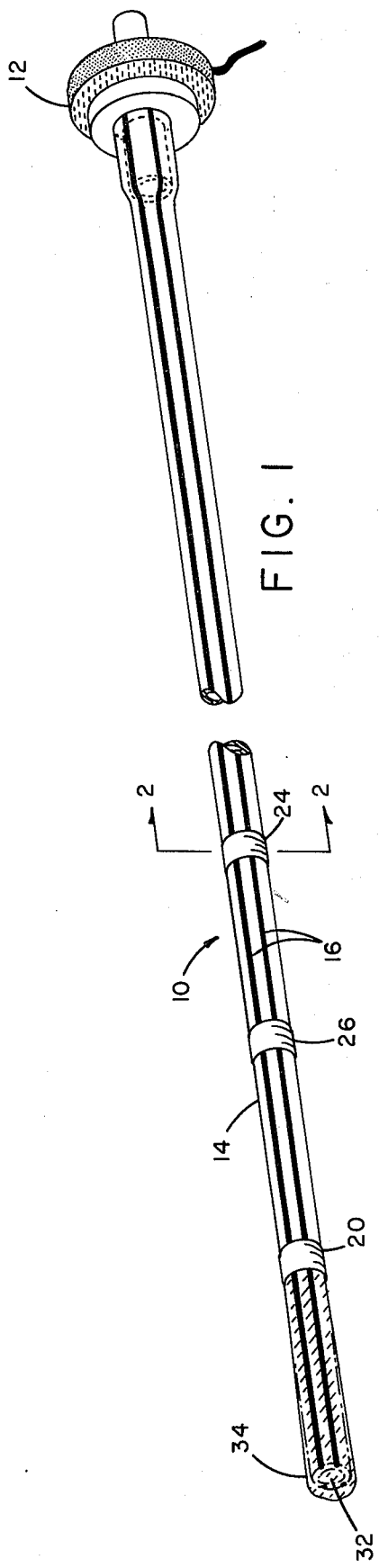
FIG. 1
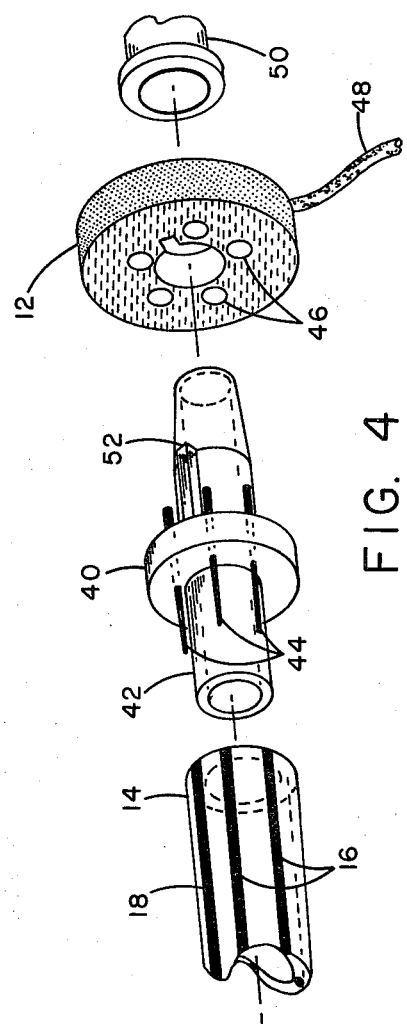
FIG. 4
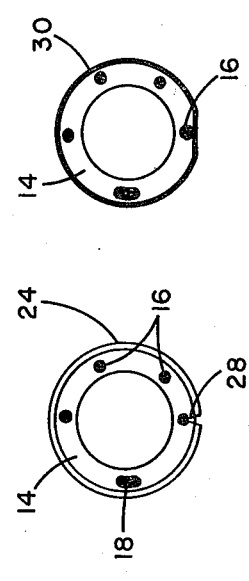
FIG. 3
FIG. 2

DISPOSABLE ESOPHAGEAL AND TRACHEAL MULTI-PROBES

BACKGROUND OF THE INVENTION

The present invention relates to esophageal probes and intratracheal tubes of the disposable variety.

Thoracic and pediatric surgical cases share common problems: the absence of suitable sites for the attachment of surface ECG electrodes; the need for continuous body core temperature monitoring; and the need to monitor heart and lung sounds. Instrumented probes have been employed to meet these clinical requirements in the past.

One example of such an esophageal probe, is shown in U.S. Pat. No. 3,951,136 to T. D. Wall. Disclosed therein is a multipurpose esophageal probe having the capability to monitor ECG, heart sounds and body core temperature. The Wall type probe has a number of deficiencies. Electrical interconnections to the ECG contacts are made via wires which pass internal to the lumen of the tube and are electrically connected at points within the lumen. When that probe is in use, it is inserted into the patient's mouth and then makes a 90° bend into the esophagus. The internal wires tend to block the lumen of the probe and distort the heart sounds which can be monitored via a stethescope attached to the proximal end of the probe. In addition, when such a probe is employed for pediatric purposes, of necessity, the probe tube must have a small diameter. Under such conditions, internal wires substantially alter the heart sounds. Furthermore, when the patient either inhales or exhales the movement of the conductors within the lumen create noise which further impairs the quality of the heart and lung sounds.

Finally, the internal wires, being comprised of an insulated metallic conductor may significantly impair the flexibility of the esophageal probe. The probe's lessened flexibility renders it more difficult for the physician to properly emplace the probe.

U.S. Pat. No. 3,499,435, to Rockwell, et. al. shows another type of probe which achieves an unobstructed lumen, by emplacing the metal conductor internal to the wall of the probe. While achieving one beneficial result, the Rockwell probe tends to sacrifice the important feature of probe flexibility by this construction, and requires at least a second external electrode to obtain ECG signals.

Conductive plastics having the requisite flexibility desired for an esophageal probe are known. However, they have the undesirable characteristic of having an extremely high resistivity unless they are heavily loaded with a conductive material (e.g., carbon). For certain purposes, a high resistivity is acceptable, e.g., a grounding stripe exposed to the exterior of the probe—see U.S. Pat. No. 3,070,132 to Sheridan. However, to achieve reasonable conductivity, the plastic must be loaded with so much conductor that if it is exposed to the patient, it is likely that the conductive material will leach out into the patient—an obviously undesirable result.

Accordingly, it is the object of this invention to provide esophageal and tracheal probes which are both flexible and disposable.

Another object of this invention is to provide esophageal and tracheal probes which are inexpensive and are characterized by an unobstructed lumen.

A further object of this invention is to provide esophageal and tracheal tubes with the necessary flexibility and unobstructed air way and which also provide a means for obtaining ECG signals, body temperature, and either heart and breath sounds or respiratory rate.

BRIEF DESCRIPTION OF THE INVENTION

The invention herein described utilizes an elongated plastic tube which has embedded in the walls thereof, vinyl/carbon conducting pathways. The distal end of one version of the tube contains a thermistor or other temperature measuring integrated circuit connected to conducting vinyl/carbon pathways. Completely enclosing the distal end is a latex membrane. At least a pair of conducting rings are emplaced on the exterior of the tube and provide ECG contacts. Several methods for making interconnection between the rings and the internal conductors are disclosed. The proximal end of the tube terminates in a plastic interconnector which is also part of the disposable assembly. The tracheal version of the tube does not utilize the latex membrane closure.

A BRIEF DESCRIPTION OF THE DRAWINGS

FIG. 1 is an isometric view of the esophageal probe.

FIG. 2 is an enlarged cross-sectional detail taken on a plane passing along line 2—2 in FIG. 1.

FIG. 3 is an enlarged cross-sectional detail of an alternative ECG contact ring.

FIG. 4 is an exploded view of the proximal end of the probe showing the details of the electrical interconnections.

Figure 5:
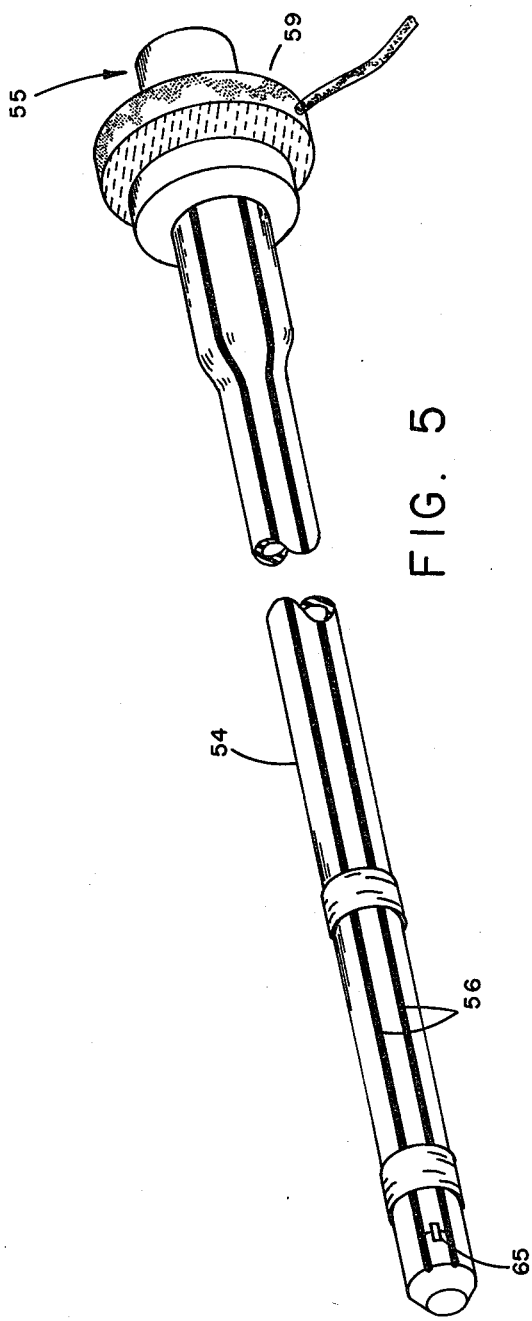
FIG. 5 is an intra-tracheal breathing tube of similar extruded construction.
Figure 6:
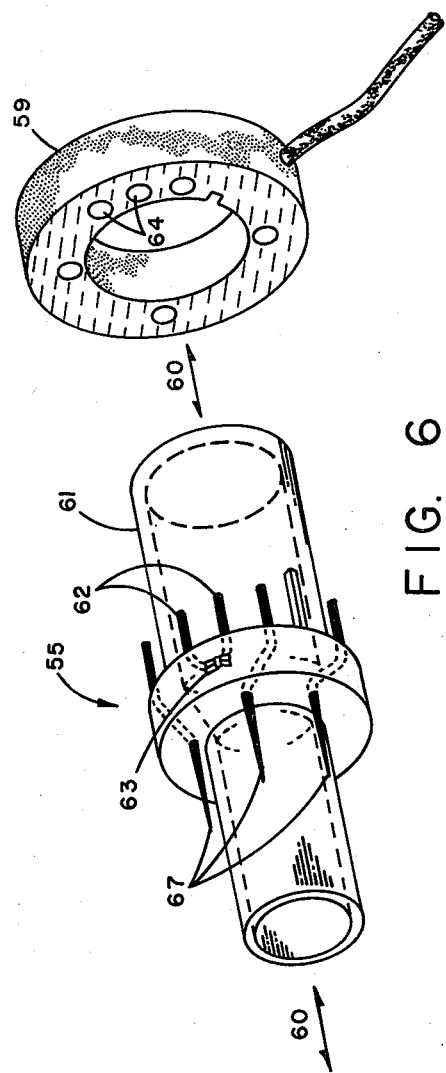
FIG. 6 is a detail of the connector plug showing the thermal respiration detector.

Referring now more particularly to FIG. 1, the esophageal probe comprises two main components tube portion 10 and interconnector portion 12. Tube portion 10 is comprised of an elongated plastic tube 14 comprised preferably of polyvinylchloride. Standard PVC surgical quality extruded tubing is satisfactory. Totally embedded within the wall of tube 14 are a plurality of longitudinal conductive pathways 16 which are of equal flexibility to tube 14. This structure is shown in section in FIG. 2. Each pathway is comprised of a carbon-filled vinyl which is co-extruded during the extrusion of tube 14. Each conductive pathway 16 can be heavily loaded with carbon due to the fact that it is completely enclosed and insulated by the wall of tube 14. This enables the resistivity of the conductive pathways to be kept quite low (i.e., on the order of 3,000 ohms per foot or less). Conductive pathways 16 are all of identical cross-section with the exception of pathway 18 which is used for alignment purposes.

Stainless steel or other bio-compatible material, ECG electrodes 20 and 24 are attached to the exterior of tube 14. Referring to FIG. 2, electrode 24 is interconnected with one of the pathways 16 via retaining cleats 28 which puncture the PVC surface of tube 14 and enter pathway 16 upon the emplacement of the electrode.

An alternate ECG electrode arrangement is shown FIG. 3. A carbon impregnated heat shrinkable vinyl collar 30 may be slipped over tube 14 and heat shrunk thereupon. Interconnection is made to one of pathways 16 by scraping away a portion of the PVC insulation prior to heat shrinking.

Optional conductive collar 26 is a common ground return and is also interconnected to one conductive stripe 16.

At the distal end of tube 14, a thermistor or other temperature measuring integrated circuit 32 is emplaced and interconnected between a pair of conductors 16 via cleats (not shown). The effective impedance of thermistor 32 must be substantially higher than the impedance of pathways 16 to enable small temperature variations to be sensed. The entire end of the tube is enclosed by a thin latex membrane 34. Membrane 34 serves two functions; it has a low acoustic loss and allows heart and lung sounds to be transmitted via the open lumen and optional acoustic ports (not shown) in the wall of tube 10 and it further prevents body fluids from entering the lumen. Membrane 34 is retained upon tube 10 by the attachment of electrode 20.

Electrical connections to tube 14 and its internal conductive pathways 16 are provided by connector assembly 12 which is shown in greater detail in FIG. 4. Disposable portion 40 of connector assembly 12 includes flanged plastic tube 42 (e.g. made of polystyrene) around the periphery of which are mounted a plurality of conductive pins 44 which are pointed at one end. A non-disposable female interconnector 46 fits over tube 42 and interconnects each of pins 44 with output cable 48. Female "Leur" connector 50 affixed to physician's stethescope engages male "Leur" fitting 42 integral with plug 40.

Interconnection between conductive pathways 16 and pins 44 is made when tube 14 mates with tube 42, thereby allowing pins 44 to penetrate conductors 16. Alignment conductor 18 is caused to mate with the interconnecting pin 44 which is aligned with keyway 52.

In FIG. 5, there is shown an intra-tracheal breathing tube 54 of substantially similar construction to the probe of FIG. 1 except that rubber sheath 34 has been removed to provide an unobstructed breathing pathway to interconnector 55.

Interconnector 55 provides through air flow path 60 with port 61 suitable for connection to standard respirator or ventilator fittings. A rapid response thermal detector such as an Analog Devices 590 integrated circuit temperature chip 63 detects respiratory flow 60. The chip is internally connected to plug pins 62, and signals are transmitted to ancillary apparatus by the mating of 62 with female sockets 64 in receptacle 59. Body temperature sensor 65 mounted in the outer wall of tube 54 is connected to two of the multiple conductive stripes 56. At assembly of tube 54 with connector 55 stripes 56 engage pins 67 forming an electrically conductive circuit.

What is claimed is:

1. A disposable esophageal probe comprising a flexible plastic tube having proximal and distal portions and an unobstructed lumen, said tube adapted to be inserted into a patient's mouth and then into the esophagus:
   a plurality of conductive pathways longitudinally embedded in the wall of said plastic tube, said pathways having substantially similar flexibility to said plastic tube and being insulated from each other and the patient by the plastic of said tube;
   at least a pair of conductive bands encircling said tube's distal portion, each band making contact with at least one embedded conductive pathway and being adapted to receive ECG signals and
   a connector plug mounted on the proximal portion of said plastic tube, said connector plug having a plurality of sharp metal connecting pins which pierce and electrically connect to said conductive pathways, said plug further having an unobstructed lumen which mates with the lumen of said tube.

2. The invention as defined in claim 1 wherein each of said pathways comprises a vinyl impregnated carbon conductor.

3. The invention as defined in claim 1 further including a diaphragm sheath of latex over the lumen at the distal portion of the tube.

4. The invention as defined in claim 1 further including a temperature sensing element capable of transmitting a signal by means of said conductive pathways, said sensing element connected between at least a pair of said conductive pathways and positioned at the distal portion of said tube.

5. The invention as defined in claim 1 wherein said connector plug includes an additional interconnecting portion which mates with said connecting pins, but is demountable therefrom, to make connection between said connecting pins and external monitoring circuitry.

6. The invention as defined in claim 5 further including a temperature sensor mounted within said connector plug and communicating with respired air which passes adjacent thereto to provide a signal equated with the movement of the air.

* * * * *